United States Patent
Christiansen et al.

(10) Patent No.: US 9,161,679 B2
(45) Date of Patent: Oct. 20, 2015

(54) IMAGE PROCESSING SYSTEM HAVING AN ADDITIONAL PIECE OF SCALE INFORMATION TO BE PROCESSED TOGETHER WITH THE IMAGE INFORMATION

(76) Inventors: Olaf Christiansen, Potsdam (DE); Eckhard Löhde, Berlin (DE)

( * ) Notice: Subject to any disclaimer, the term of this patent is extended or adjusted under 35 U.S.C. 154(b) by 718 days.

(21) Appl. No.: 13/391,446

(22) PCT Filed: Aug. 17, 2010

(86) PCT No.: PCT/DE2010/050058
§ 371 (c)(1),
(2), (4) Date: Sep. 21, 2012

(87) PCT Pub. No.: WO2011/020471
PCT Pub. Date: Feb. 24, 2011

(65) Prior Publication Data
US 2013/0194404 A1    Aug. 1, 2013

(30) Foreign Application Priority Data
Aug. 18, 2009  (DE) .......................... 10 2009 038 021

(51) Int. Cl.
H04N 7/18      (2006.01)
A61B 1/04      (2006.01)
A61B 1/00      (2006.01)
A61B 1/05      (2006.01)

(52) U.S. Cl.
CPC .............. *A61B 1/00009* (2013.01); *A61B 1/05* (2013.01)

(58) Field of Classification Search
CPC .............................. A61B 1/00009; A61B 1/05
USPC ........... 348/67, 136, 135, 138, 140; 356/3.11, 356/4.03, 603, 606, 625, 626, 627, 628, 356/629; 600/108, 109, 160, 168
See application file for complete search history.

(56) References Cited

U.S. PATENT DOCUMENTS

| | | | |
|---|---|---|---|
| 3,817,635 A | * | 6/1974 | Kawahara ..................... 356/625 |
| 3,995,287 A | | 11/1976 | Storz |
| 4,396,944 A | | 8/1983 | McKenney |
| 4,621,284 A | * | 11/1986 | Nishioka et al. ................ 348/69 |
| 4,834,070 A | | 5/1989 | Saitou |
| 4,852,567 A | | 8/1989 | Sinofsky |

(Continued)

*Primary Examiner* — John Villecco

(57) ABSTRACT

The invention relates to an image processing system, containing an optical digital camera (1) having means (4) that produce information representative of a specified geometric distance within the image using laser light in the detection range of the optical digital camera (1), said information representative of the specified geometric distance being processed together with the image information. Separating means (8) are arranged downstream of the digital camera, said separating means separating the information representative of the specified geometric distance from the image information. Subsequent evaluating means produce a distance value therefrom. Image storage means (9) additionally arranged downstream of the separating means are used to store the recorded image information. Adjustment means (14) automatically change the image size on a display in the form of a digital zoom for the purpose of setting the reproduction size according to a specified scale factor in such a way that an object contained in the image content, the physical dimension of which object corresponds to the specified geometric distance, is reproduced in a corresponding dimension that is multiplied by the specified scale factor.

13 Claims, 4 Drawing Sheets

(56) References Cited

U.S. PATENT DOCUMENTS

| | | | |
|---|---|---|---|
| 4,980,763 A * | 12/1990 | Lia | 348/67 |
| 4,986,262 A | 1/1991 | Saitou | |
| 5,150,254 A | 9/1992 | Saitou | |
| 5,200,819 A | 4/1993 | Nudelman | |
| 5,207,494 A | 5/1993 | Jones | |
| 5,633,675 A * | 5/1997 | Danna et al. | 348/65 |
| 5,669,871 A * | 9/1997 | Sakiyama | 600/117 |
| 5,807,242 A | 9/1998 | Scheller | |
| 5,882,294 A | 3/1999 | Storz | |
| 5,967,968 A * | 10/1999 | Nishioka | 600/117 |
| 6,106,456 A | 8/2000 | Storz | |
| 6,184,923 B1 | 2/2001 | Miyazaki | |
| 6,221,007 B1 | 4/2001 | Green | |
| 6,367,958 B1 | 4/2002 | Jones | |
| 6,388,742 B1 | 5/2002 | Duckett | |
| 6,409,391 B1 | 6/2002 | Chang | |
| 6,454,762 B1 | 9/2002 | Rösler | |
| 6,468,202 B1 | 10/2002 | Irion | |
| 6,498,642 B1 | 12/2002 | Duckett | |
| 6,503,195 B1 | 1/2003 | Keller | |
| 6,824,539 B2 | 11/2004 | Novak | |
| 7,108,657 B2 | 9/2006 | Irion | |
| 7,134,992 B2 | 11/2006 | Schara | |
| 7,170,677 B1 | 1/2007 | Bendall | |
| 7,206,006 B2 | 4/2007 | Nah | |
| 7,232,409 B2 | 6/2007 | Hale | |
| 7,257,772 B1 | 8/2007 | Jones | |
| 7,381,183 B2 | 6/2008 | Hale | |
| 7,389,473 B1 | 6/2008 | Sawicki | |
| 7,486,805 B2 | 2/2009 | Krattiger | |
| 7,689,014 B2 * | 3/2010 | Abovitz et al. | 382/128 |
| 7,821,649 B2 | 10/2010 | Bendall | |
| 8,663,092 B2 * | 3/2014 | Pascal et al. | 600/117 |
| 2002/0054048 A1 * | 5/2002 | Nah et al. | 345/698 |
| 2003/0202120 A1 | 10/2003 | Mack | |
| 2004/0127785 A1 * | 7/2004 | Davidson et al. | 600/407 |
| 2004/0242961 A1 * | 12/2004 | Bughici et al. | 600/108 |
| 2005/0177312 A1 | 8/2005 | Guerrant | |
| 2005/0240077 A1 * | 10/2005 | Rovegno | 600/108 |
| 2006/0290781 A1 * | 12/2006 | Hama | 348/135 |
| 2007/0065002 A1 | 3/2007 | Marzell | |
| 2007/0161854 A1 * | 7/2007 | Alamaro et al. | 600/109 |
| 2007/0197873 A1 | 8/2007 | Birnkrant | |
| 2007/0208252 A1 | 9/2007 | Makower | |
| 2008/0009674 A1 | 1/2008 | Yaron | |
| 2009/0247824 A1 * | 10/2009 | Kawasaki et al. | 600/109 |
| 2010/0091104 A1 * | 4/2010 | Sprigle et al. | 348/136 |

\* cited by examiner

IMAGE PROCESSING SYSTEM HAVING AN ADDITIONAL PIECE OF SCALE INFORMATION TO BE PROCESSED TOGETHER WITH THE IMAGE INFORMATION

BACKGROUND OF THE INVENTION (a) Field of the Invention

The invention relates to an image processing system for image data in endoscopy, which is especially useful for surgical purposes but may also be used in general technology.

(b) Description of the Related Art

Such image processing systems in the form of digital endoscope cameras are in use both in general technology with respect to hardly accessible repair positions—as well as in minimally invasive surgery. Due to the short focal length of the cameras, a relatively large depth of field is provided, which is necessary to provide a good overview of the workspace. So the objects under inspection do not get out of focus with a displacement of the endoscope. The cameras have a fixed focus which is adapted to the working area. The depth of field in known systems may comprise a distance from 1 mm to infinity.

The objects under observation and in focus within a working area may be located at different distances from the camera front lens. The size of an object displayed on the monitor is difficult to evaluate if there are no close objects of known size available in the picture.

The system known from U.S. Pat. No. 7,206,006 B2 for representation in actual size by means of a digital camera and a corresponding display may not be used for the intended application. A pre requirement for the known system is a fixed distance between the object and the lens of the camera. Furthermore, frame synchronization pulses have to be inserted in the picture as a size reference. It is apparent that these reference pulses do not change with the distance of the object—and therefore with the reproduced size. With the variation of the object distance the reproduced object changes in size, without any recognition of the change of scale, because the number of frame synchronization pulses is not varying accordingly.

A quite different situation is to be found in picture representations in medical technology gained by direct X-ray radiation or by computer or Nuclear Magnetic Resonance Spectroscopy. Here the scale is already set by the picture geometry used (which may be natural scale). This indeed provides processes for the virtual adaptation of implants to the patient, for example in dentistry. An example is shown by VIP Virtual Implant Planning, at: http://www.virtual-implant.de/simulation.html (available date of priority). Here are three dimensional image representation renderings of CT and implant are fitted by manual selection, overlaying and spatial displacement. This method therefore is also unsuitable for the above-described problem. In addition, the imaging, the selection of the implant, the orientation and assessment by the operator has to take place remote from the working field and is time consuming. That is why the known procedure may not be used during surgery. The same applies to a planning software for dental implants, http://www.materialise.com/materialise/view/en/131410-SimPlant.html, that has also been accessible before the application's priority date.

From EP 1778094 B1 an endoscopic video measurement system is known, by means of which light points in the range of the object may be generated to carry out measurements within the image representation. This measurement is performed by manual selection of suitable points and the subsequent determination of the scale by means of selected distances measured within the image representation. Subsequently a detail in the image representation is selected, whose dimension is to be determined. After having determined measured manually the relevant details in the picture, its dimensions may be calculated on the basis of the scale factor and the unit of measurement selected. The Dimensions of an implant or repair element to be introduced to the field has also to be known to fit. The fit may be judged only on the basis of the two metrics. This procedure is cumbersome and unsuitable for a rapid handling during surgery.

The foregoing system may be used appropriately in the event of medical imaging, as described in http://www.efims.de/de/meetinRs/hnod2009/09hnod324.shtml. According to this method by means of manually determined distances defined by the laser markings the volume of the object may be estimated. This procedure is also time consuming and therefore cannot be performed during surgery. In the known solution is the image representation scale on the monitor stays fixed. That is why a direct comparison with a physically present object or an image representation stored as a reference element in a fixed scale is not possible.

In a system describe in U.S. 2007/0065002 A1 by means of which a recorded 3D laser scan data model may be updated with 2D image representations is also not giving any evidence.

In JAHNKE, M. 3D exploration of volume data, thesis, Univ. Bonn, 1998, general tools for subsequent interactive exploration of medical image representation data are described. Notes respective to image representation reproduction in scale during surgical application do not apply.

In the lecture notes VORNBERGER, O., MUELLER, O.: Computer Graphics, Univ. Osnabruck, S S 2000, the basics of in computer graphics are described. There is no evidence with respect to present problem.

In JERAMIAS.RF: CMOS image representation sensors with short-term closure for depth sensing the principle of light transit time measurement and a method for measuring distances according to the light transit time principle is described. This kind of distance measurement however is not of direct relevance in connection with the aforementioned problem.

In GRIONI, C. Digital photography, Diploma Thesis, Univ. Graz, 2007, the Sony Smart Zoom principle is described, by means of which a digital zoom is limited to a selected resolution in order to maintain a desired playback quality. This solution also is not relevant to the problem discussed here.

SUMMARY OF THE INVENTION

The object of the invention is to provide an image processing system by means of which a surgeon or an operating person during endoscopic observation is enabled to determine the dimension of an observed item on a monitor display. Also the dimensions of an adapted repair element or implant to be inserted to the working or surgical field shall be determined quickly and directly. Thus the requirement of direct measurements in the working or surgical field under endoscopic examination is avoided. There also may be a subsequent conversion into linear dimensions. In the field of minimally invasive surgery under endoscopic observation, the times necessary for the surgical intervention may be minimized. (In the present text the usability of the invention both in general technology on one hand and the medical field on the other hand is expressed by the equating usage of the terms "working area" and "surgical field" and "repair element" or "implant" respectively.)

With the invention the image representation on a monitor display may be adjusted such that a relevant object in the scene is reproduced in a fixed scale—preferably original scale. Thus the monitored area of the scene—inaccessible to direct manual intervention—may be used to compare geometric dimensions with physical objects. The distance of a laser marking of the optical axis may be preferable used as a scale reference.

Especially advantageous in the invention is that size estimation, adaptation and selection of implants may also be performed directly in the sterile area of the operating room. Especially for minimally invasive procedures an implant may be prepared in size externally—without immediate and possibly multiple—access to the surgical field. In modern surgical techniques in the field of laparoscopy, especially for the treatment of inguinal and diaphragmatic apertures, precisely matched nets are necessary. It is shown here how nets to be transferred to the surgical field may be simply prepared with high precision and accuracy.

According to the invention, it is either possible to perform a direct comparison with respect to form and size in original scale on a working surface formed by a monitor display. This may also be done using a partial view on the display when larger objects are to be handled. In rare case in general technology also a scaled model of the element to be inserted may be used with an image representation of the working field in adequate scale. The element in original scale may later be precisely manufactured for example by means of a copying milling machine.

The present system may be used in all cases when the working field is not accessible for a direct form or size comparison with the element intended for insertion. The surgeon is thus provided with a "workbench" located outside the surgical field, by means of which he may make adjustments and adaptations outside the body. Implants and in particular nets (meshes) for laparoscopic hernia repair may be produced by accurate selection and preparation. This may be done either by use of the original specimen or by overlaying a picture representation in the appropriate scale to the reproduction of the surgical field on the monitor display. The selection of a proper repair element may also be performed automatically or semi automatically by means of a "digital catalogue", as it will be described further below.

The information representative for a geometrical distance within the image representation field of the optical digital camera preferably is defined by the center of at least one laser marking that is projected on to an object by a laser beam directed preferably in parallel to the optical axis of the camera. Such laser markings may be generated by small units, which may be readily attached within or near the lens of the endoscope. Either the distance between the centers of two laser markings with respect to each other or the distance between the center of a laser marking and the optical axis of the camera may form the representative geometrical distance information used to establish the scale factor of the relevant part of area to be observed.

The direction of the laser radiation may also be inclined with respect to the optical axis, if this distance is defined in a sense that for each object distance of the location of incidence of the laser beam is determined, so that after detection of the laser marking a geometric distance as the reference distance may be calculated with the aid of the lens equation. By means of the optical axis, which forms the center of the image representation, and laser beam of defined direction relative to the optical the scale of an image representation of an object at the impact of the laser beam may be calculated.

In a favorable embodiment multiple laser beams are arranged around the optical axis of the camera, in a preferably evenly distributed circular arrangement. Then for scale determination particularly those laser markings are selectable for exclusive further processing, which are in defined symmetrical arrangement with respect to their neighboring markings as well as the optical axis. Thus it may be secured that the calculation of the scale of a plane surface is not distorted by laser markings being positioned on recesses or projections of the object.

Even if the object plane is not in orthogonal direction with respect to the optical axis, the local scale may be detected by means of several laser markings emitted by laser beams in a defined distance from the optical axis. A different distance of two laser markings symmetrically positioned with respect to the optical axis means that the image representation of the object plane is distorted trapezoidal which may be compensated by a means keystone correction. By a corresponding equalization thus a true image representation may be produced on a flat monitor display, in which the inclination of the object plane is compensated. In general, it may be—in particular with the use a flexible endoscope this may be also achieved by the use of a camera combined with a flexible endoscope formed to direct its optical axis orthogonally with respect to the object plane. Otherwise the described method should be used utilizing the keystone correction which may even be used with more than two laser markings found in a defined position on the object plane. Making use of three laser markings any inclination of the object plane may be corrected to be displayed on the monitor screen with a uniform scale factor.

In another advantageous embodiment if the separation of the laser marking out of the picture content of the image representation contents of two consecutive recorded images during an on and an off state of laser light sources are subtracted from one another, so highlight the laser markings for analysis while rest of image representation is diminished. To enhance the reproduction of the laser markings even better during in that period, the light source for object illumination, for instance white LEDs, are shut off or reduced in intensity during that period.

A kind of "workbench" approach may be achieved if the surface for the image representation on the monitor display is extending in a horizontal direction and may be covered by a protective glass plate for the direct application of the element or implant to be inserted into the working or surgical field for comparison a direct contact in original scale.

If the monitor is formed as a separate unit in a separate enclosure with autonomous power supply and a radio interface data connection to other systems, the display unit may be easily transferred from the place of endoscopic imaging for local adaptation of the repair element or implant.

The novel imaging system is universally applicable and may be used for medical or surgical purposes as well as in general engineering, where repairs or modifications are to be made in areas inaccessible to direct manual manipulation. In this case, either especially prepared endoscopes are to be used in which laser sources are to be arranged at their object (distal) end. In conventional endoscopes having a working channel the laser source may also be positioned proximally using a light guide fiber for the laser beam extending to its distal end.

In another advantageous embodiment of the invention—digital displacement or rotation means are provided, by means of which an overlaid image representation of the captured image representation of the element or implant to be inserted into the working or surgical field respectively may be shifted or rotated in its intended position in the display plane. Thus the physical interaction of the objects may be checked with the work piece or the patient's body in the working or surgical field to be simply checked. On the other hand, however, also tests and experiments with various forms of adjustment may be made, which in this way would not be possible in the original working or surgical field.

In the image processing system may further be provided the image memory means downstream connected means for highlighting out selection of picture elements in the repair area, the selection being made according to predetermined criteria on the basis of the recorded image representation data. The selected feature image representation data forms a "region of interest (ROI)" which may be used for selective adjustment of a repair element. The corresponding area may also be used for remote processing (telemedicine) transmitted to a remote location in control of necessary actions.

When the ROI defining data may be as a selection criterion to select the color, intensity, or any other common image representation content to act, where in it the shape or dimensions of this area or the other image representation content criteria for the automated selection of the work or operating range to be introduced elements or implants may provide. As an extension of the known technique of the element or content-based image representation recognition, is in an automated selection is not just an image representation found because of its content features, but because of content or elements of the harmful image representation is a comparison with the properties of related suitable elements or content features in a database for repair elements or Implants are made in which these features of damaged areas are classified and are selectable. After the automated selection of the item for a similar comparison of the demand characteristics of the respective characteristics of the available repair elements, the appropriate be physically removed from a warehouse and placed on the monitor to be subjected to a 1:1 scale, if desired, additional manual adjustments.

By those induced by means of the relevant criteria of form, color and other feature matching is thus from an existing electronic catalogue in a memory, on the basis of the image representations stored in a selection of a suitable element or implant, giving details of the type or order number, size, etc. made. This is the comparison is performed preferably using a special description language which allows the identification of image representation features in compressed form. A suitable description language for example, is defined by MPEG7.

When used in the medical field, in particular, laparoscopic uses, in which the invention may be used in a favorable way, because there is a surgical planning by computer is between the people difficult because of the mobility of the internal organs and many decisions and adjustments directly in the operative must be made during the phase of surgical activity.

The application of the invention is not limited to positive mold members only. An advantageous embodiment also makes use of negative forms (templates), with the cutouts in the limited workspace template may contain or reference elements in the form of printed characters, which facilitate the operation of a surgeon or a fine mechanic.

According to another form of positive elements are conveniently producible or selected, for example, a substrate layer with an adhesive surface may be produced for later repair. This may be provided that the layer to effecting adhesion dissolves in a time dependant process.

An advantageous embodiment of the invention is shown in the drawing in detail and will be described in detail below.

DETAILED DESCRIPTION OF THE INVENTION

The function of the novel image processing system shown in the block diagram of FIG. 1 will now be explained on the basis of a medical application. An image representation of the surgical workspace is provided by an endoscope camera 1. The output signal from the endoscope camera 1 is fed to a frame buffer 2 memorizing the last frame of a video signal, which is recorded in a progressive-scan method. Thus for subsequent data processing the last actual image is available, which will be displayed on a monitor 3, under continuous observation forming a video sequence.

Figure 3A:
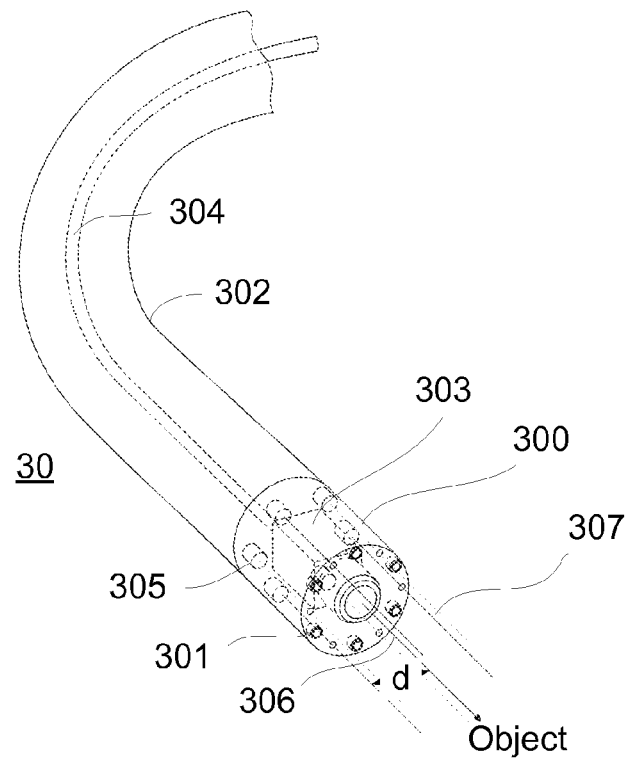
FIG. 3a is a perspective view of a first embodiment of an endoscope with a camera making use of the invention.

Next to the lens of the endoscope camera 1 a laser light source 4 is mounted generating several laser beams which are directed in parallel to the optical axis of the camera. (The spatial arrangement is represented in FIG. 3a in more detail and will be described further below.) The laser light bundles are projected in fixed distances. They generate an information representative for a geometrical distance on the object which is independent of the object distance and is going to be processed together with the image information of the camera 1.

Instead of a laser light beam the optical axis of the camera may also be used as geometrical reference. The processing is performed in nearly identical form, independent of the fact whether the geometrical distance information has been derived from two laser markings or one laser marking and the projection point of the optical axis on the object.

On the object in the surgical field for example two laser markings are produced that appear in the camera image. This distance in the image representation—although fixed on the object—is varying with the distance between the camera and the object. Depending on the focal length of the lens of the camera the distance between the laser markings in the image decreases rapidly with the increasing distance of the camera from the object thus forming a reference for the scale of the image of the object on the monitor 3. Accordingly several laser beams may be used which encircle the optical axis of the camera in a symmetric arrangement. (The laser light beams may also have a defined (non parallel) angular direction with respect to the optical axis. By means of the geometrical relationships and the lens formula the position of each laser marking being reproduced on the object is representing a scale information with respect to the of reproduction of the region of the object the laser marking is placed on.)

For a direct comparison of an implant to be inserted into the surgical field the scale of reproduction is set to 1:1 (original scale). Form and size adjustments of the implant may be made by placing the object directly on the screen of monitor 3. For larger objects, that exceed the dimensions of the front surface of the monitor 3, a smaller scale reproduction of the object may be chosen. In this case an alignment is done with a stored image representation of the surgical field in an adequately reduced scale. To finish the processing of the implant the scale of reproduction may later be changed to original (1:1) size, in order to align a portion of the actual implant for comparison on the monitor with the respective region of the surgical field.

Figure 2:
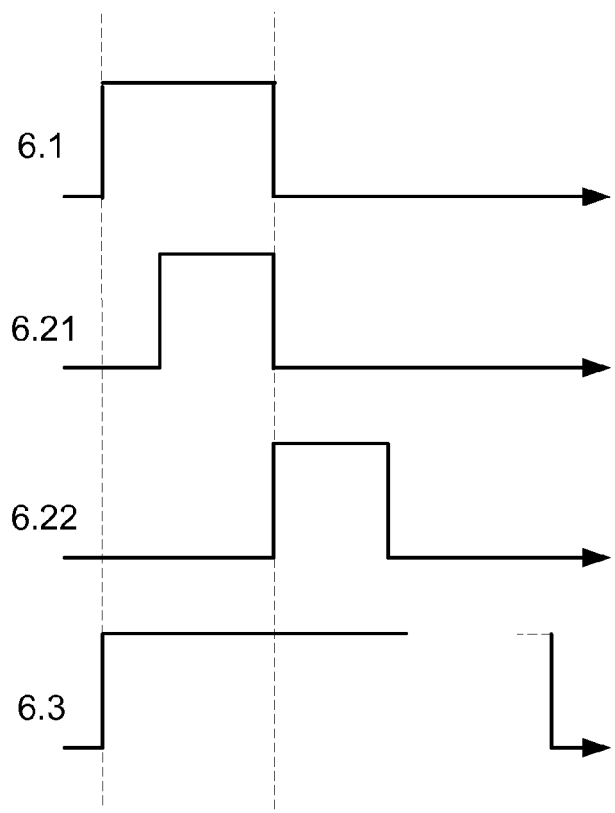
FIG. 2 is a diagram with various pulse signals explaining the operation of the system according to FIG. 1.

The laser light source 4 is fed by a driver stage 5, which is controlled by a timer unit 6. Control pulses 6.1 and 6.2 are supplied at the output of the timer unit 6, each of which is forming a sequence which is manually activated for a sequence by a trigger element 7. This and the following pulse signals of the sequence are shown in detail in FIG. 2. The trigger 7 is bistable and by every second input pulse a "hold" output pulse 6.3 is generated until its input is subsequently activated again. This pulse 6.3 is used to transfer the most recent image from the camera 1 which is held in the image buffer 2 to the image memory 9 which is downstream connected. The image will persist in the buffer 2 as a still image until the bistable trigger 7 is activated again.

Until the start of the pulse sequence the output of the camera 1 remains connected to the monitor 3 and a continuous video sequence from the object under observation is delivered by the camera 1 which thus may be controlled in its position with respect to the object by the operator. The trigger 7 is enabling a sample and hold function. Its activation element may be conveniently positioned in the operating panel of the endoscope camera, or may be linked to the output signal of the trigger button of the camera for shooting and recording a still picture—which is not shown in the figure.

The inverted hold signal 6.3 of the timer 6 additionally is passed to a driver stage 10 for a light source 11 for the object, which consists of a number of white LEDs. During the normal reproduction of the actual video information the light source 11 is on, the object being illuminated until the last frame of the video sequence is held as a still image. With the release of the hold signal 6.3 the light source (LED) 11 is being switched off. Thus the laser markings may be evaluated with greater accuracy without any disturbing additional illumination.

The sequence of pulses 6.1 to 6.22 is used to control the evaluation of the image caused by laser light source 4, which is processed and displayed on the monitor 3. In a sequence, first an image of the view is recorded by means of a separation unit 8 with the LED light source (Pulse 6.21) being switched-off (Pulse 6.3) while the laser light source is activated (pulse 6.1). Immediately after switching off the laser light source, the actual image is subtracted from the previously captured image held in the memory by the pulse 6.22 in a in the separation unit 8. Since this is an image of the non illuminated scene (LEDs and laser source are in off state) the remaining image in the memory will be the laser markings produced the laser source 4 as the sole content of the image representation signal. For precise evaluation the center of the laser marks are geometrically determined by a center of gravity and/or an intensity criterion by means of which the area of the greatest brightness of the laser marking is assigned its center.

In the case of the evaluation of the images of two laser beams two laser markings are contained within the image recorded by the camera whose centers having a distance which a is corresponding to a fixed distance d on the object. The corresponding image representation data is transferred to be held in a distance detection memory 12. The determined centers of the two laser markings, i.e. their geometric centers—are derived in Cartesian coordinate values (from the position of the corresponding pixels in the image representation memory and in accordance with Pythagoras from the distance of the respective coordinate differences, the length of the hypotenuse is determined as the distance in the picture area (in pixel sizes of recorded image). Additionally a system-specific multiplier is used that takes into account the ratio of the size of the physical monitor size and its pixel numbers, that in case of a reproduction in original (1:1) scale the objects of interest of the working or surgical field will appear in actual size. When using the optical axis of the camera instead of a laser beam the intersection of this optical axis—i.e. the coordinates of the image representation center point (0, 0) is evaluated instead of the center of a second laser marking.

In the case of several laser markings surrounding the center in a symmetrical pattern, only those are evaluated, which do not to deviate by more than a predetermined amount from the pattern surrounding the optical axis of the camera—i.e. the center of the image. The position data of the remaining markings are then averaged and at least one distance value or the average distance values for several centers of the image representation are passed on to determine the scale factor.

To produce a 1:1 display on the monitor 3, the distance value obtained is divided by the real geometric distance d of the laser light sources 4. The respective calculation is performed in a scale multiplier 13. The output of this multiplier 13 is passed on to a unit for the adjustment of the image representation size 14, which provides an electronic zoom function. At the output of the unit 14 thus appears the normalized image representation signal, which is transferred to the monitor 3 for display. An image on the monitor display in original (1:1) scale is produced, thus enabling a direct assessment of the work area in the still image representation, so that on the monitor or a glass plate mounted thereon is forming a working surface. All manipulations and adjustments of the element to be inserted to the working area may be performed here in a model situation which cannot be performed with respect to the original working field because of its inaccessibility. Customized cuts and shapes and elements may thus be adapted to the working area in direct manipulation. This applies in particular to repair items or appropriate elements.

If—for example, for a better overview—a larger section of the working field is to be displayed, an additional switch 15 for the external scale setting the value of 1:1—according to the basic position of the switch 15—may be overrun, thus enforcing the presentation of the working field on the monitor 3 in a different scale. This is accomplished by overriding the factor from the scale setting 15 in the scale multiplication section 13 with a different value. This is of importance if a reproduction different from original (1:1) scale is desired.

Figure 1:
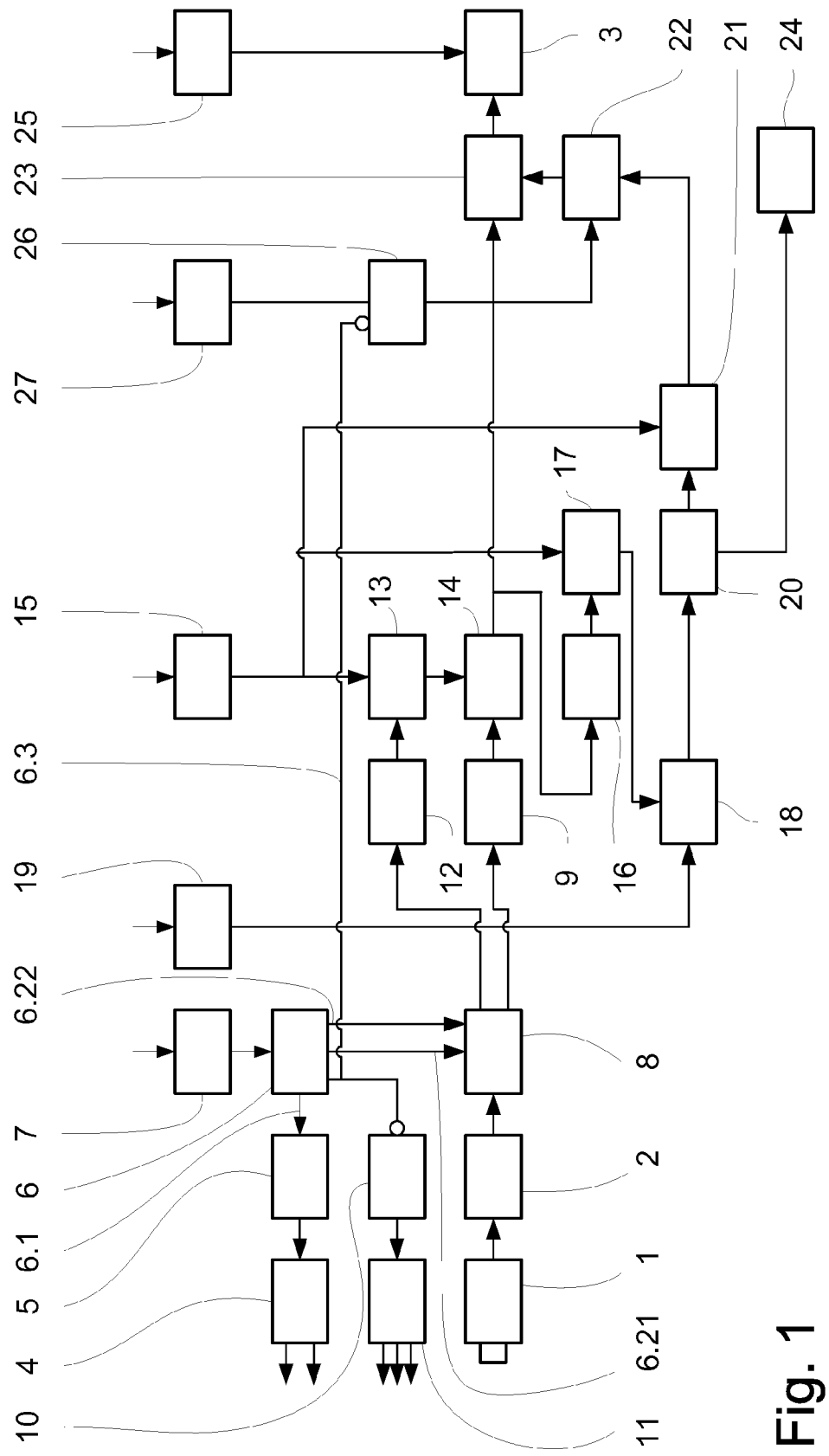
FIG. 1 is a block diagram displaying shows the general functioning of the inventive system.

In the in system according to FIG. 1 further means are shown, which allow in case of the intended fixing of a damaged area in the working field to select a repair item which has an appropriate size and shape and is adapted in its other properties to the kind of damage. In the case of the laparoscopic treatment of a hernia defect this means that a medical net of suitable size and shape has to be selected or produced. In the case of damage inside a container in general technology which is not directly accessible this may mean, for example, to select a repair kit of suitable corresponding size that may be fixed by laser welding. In other applications, working drafts or patterns or adhesive bond structures of repair materials in original size may be prepared. These means will be further illustrated in detail below.

Downstream connected to the unit for adjustment of the image representation size 14 is a form discriminator 16 that—starting from the center of the image representation display elements is selecting adjacent pixels within a window of similar characteristics (intensity, color, pattern connection) to be discriminated and labeled accordingly. Subsequently, a form of smoothing and a compactness criterion is applied, which includes pixel elements that are located within a closed defect area to be treated as a typical form for by a common procedure. The form discriminator is suitable, for example, to include areas with similar colors to be selected and presented in a closed-form area. This form field may then be used in his presentation on the monitor as the basis for the development of a template or an implant. Secondly, the shape may also be further processed "virtually" to serve as the basis for the selection of a suitable repair element from a catalogue.

The thus obtained highlighted form element within a uniform closed field structure is subjected to an adjustment in size in a size correcting unit 17 according to the using the scale setting switch 15 set scale (if this is not 1:1), so that the determined form corresponds to the size of the repair area in the working field—even if this is beyond the size of the monitor 3 in original (1:1) display. This area is called ROI (region of interest) and is representing graphically, the defected working area in schematic form, so that due to these data, a shape comparison with memory organized as a catalogue may be performed. In this catalogue memory representations of fixing elements sorted according to features like form, model, type and illustration are stored.

By a comparison unit 18, being downstream connected, a repair element of a suitable form may be selected from a given stock by means of the catalogue. For the shape comparison various mathematical methods may be used, such as the recognition of the similarity in shape by minimizing rectangles between the molds to be compared, as being state of the art. This may be performed on the basis of stored pixel representations. In the illustrated embodiment, it is assumed however that the comparison is being performed with the use of a representation of graphic elements in a compressed form making use of a comparison using selection criteria on the basis of labeling methods, such as are for example, standardized in MPEG7. The selection process uses the element or content-based image representation recognition in such a way that the image representation of the repair area with a damage of certain shape and color and features of size are assigned being characteristic for the particular application. The repair elements or implants are associated with these featured elements as selection criteria. Thus an appropriate repair element may be automatically selected on the basis of necessary visual features for the actual task being detected from the representation of the defected area and transformed into features of the repair element to be selected.

A manual selection function, represented by a selection switch 19 includes form additional selection criteria or additional selection characteristics for the element to be performed manually. A selection signal with the overall shape data catalogue storage elements 20 is fed as input signal. In this elements catalogue memory 20 all recorded elements for the application under consideration elements are stored with an image representation.

Here with respect to each repair element at least two image representations are held, each of which represents a realistic representation as a kind of an image (for example in the form of JPEG data), while the other contains structural factors (i.e. image representation content-related) type and serves for comparative purposes in the selection process. Here preferably only shape features are stored, the features, these correspond to the selected shape corresponding damaged area to be compared. A coding takes place according to the MPEG7 standard, so that when the mold compared to features are compared as digital values. It is required, that in addition in the form of discrimination in form discriminator a data compression in the way which is not that the pixel data is stored, but the description thereof with the parameters set by the compression method "data words", which is then formed into the corresponding the repair element descriptive data words be adjusted. This simplifies the comparison shape substantially in the unit 18. The size of the correction unit 17 is then limited only to a change of size notation, so forms elements stored in the memory elements must only be recorded in a general form of representation which is independent of individual size.

By the selection signal, the appropriate element selected in image representation and a latch 21, a switching unit 22 and a superimposing unit 23 to the current in the monitor 3 displayed image representation superimposed added, keeping the covers on the monitor 3 shown workspace by the image representation of the added element.

To ensure that the representation of the selected element corresponds in its dimensions and the scale of the work area, which is scaled by the elements 20 to the memory catalogue monitor 3 output image representation data corresponding to the external standard set at the setting 15.

To inform the operator by the element catalogue store 20, the type designation of the selected element to a corresponding display unit for the element type of element 24 is presented, which is in the practice in monitor 3 Enter ID, as shown below in more detail.

For the matter of clarity, here again the principles of the automated selection of a repair element (implant) will be described again as a kind of flow diagram, which is not bound to an endoscopic application:

1. The selection of the repair area due to selection of corresponding image representation features in a contiguous area (ROI).

2. The content-based analysis to find characteristic (visual) image representation features within the ROI included the measurement according to the characterization of image representation files in preparation for content-based image representation retrieval.

3. The summary of the image representation features relevant to the repair field image representation features to request properties for the repair element selection in the database.

4. The forming of the combined image representation features as selection criteria for addressing the database in which the elements are sorted according to these criteria.

5. The reading of the model number with image representation file and the transfer the image representation file to the monitor The display on the monitor 3 may be controlled by means of a display selection switch 25 between the pure representation of the workspace on the one hand and a superimposition of the captured image representation with the selected ROI (Region of Interest) or the selected element or repair implant on the other hand. This representation selection and overlay is suppressed by an AND gate 26 having an inverting input if the video function on the monitor 3 is enabled by the timer 6. The corresponding signal at the inverting input of the AND gate 26 from the timer unit 6 will also turn off the illumination 11.

By means of a position switch 27 the position of the element may be moved with respect to the working field on the monitor in order to optimize the adaptation.

If the scale setting 15 is set from a scaled-down reproduction to original (1:1) scale, then the element may be displayed only partially, if its dimensions exceed those of the monitor 3. In this case, an adaption is to be performed within the limited area of display only.

At the embodiment reproduced in detail in FIG. 3a at the of a camera head 300 of an endoscope 30 at the end of the flexible endoscope tube 302 a camera 303 is mounted with a fixed focal length (as the image recording medium endoscope camera 1 of FIG. 1). A number of laser light sources 305 are positioned around the optical axis 306 at predetermined distances d to produce laser light beams 305 in parallel from to the optical axis 306. The electrical leads are guided within a cable 304 in the interior of a sleeve 302 of the flexible endoscope. Furthermore next to the camera body 503 bright white LEDs 301 are provided directed to illuminate the object. They are supplied with electric energy by a cable 304.

On the object laser markings are produced by the laser light beam 307 whose distance d on the object is independent of the distance of the camera lens to the object, since the laser beams are directed in parallel and have a substantially constant cross section. The laser markings produced on the object are selected for further processing depending on their matching the distance from the optical axis 306, to make sure that the selected areas for scale calculation on the object in, are matching in distance with respect to the camera lens has, which is characteristic of the work area. Laser markings with a deviating distance from the optical axis in the image will be suppressed in the averaging process for producing the distance value for calculating the scale factor.

Figure 3B:
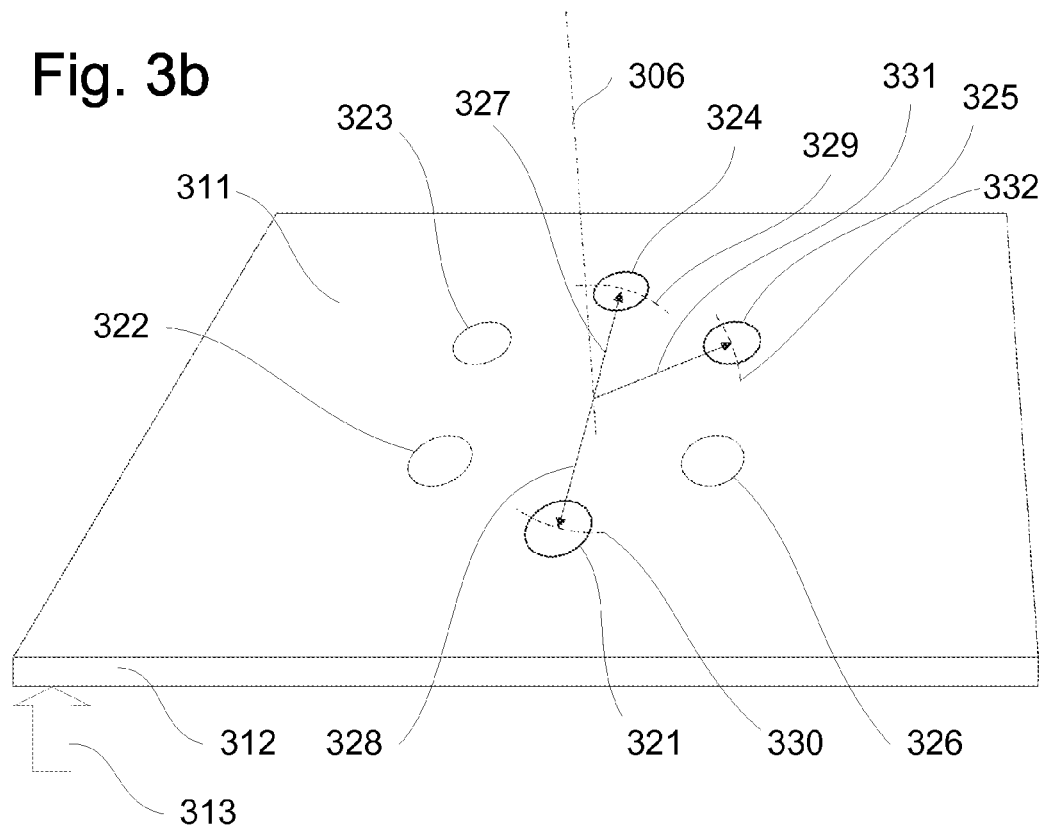
FIG. 3b is a perspective view of a measuring process with an endoscope according to FIG. 3a, with the object plane being arranged in a non orthogonal direction with respect to the optical axis of the camera.

In the case of FIG. 3 in reproduced schematic diagram illustrates, as may be given with an endoscope and the described circuit means a plane on a 1:1 scale again, which is not directed orthogonally with respect to the optical axis 306 of the camera (FIG. 3a) in the endoscope 30. The camera 303 is directed to a square metal plate 311 shown in FIG. 3b, which is raised with respect to the plane of the paper at the edge 312 facing the observer in the direction of arrow 313 so that here a distance to a plane which is orthogonal to optical axis is directed 306. The six laser light sources 301 (FIG. 3a) generate six laser markings 321 to 326 on the plate 311 (FIG. 3b) in the form of small discs. For the type shown in FIG. 3, the inclination tendency it would be sufficient to select two laser markings 321 and 324, as they are positioned in the direction of the maximum slope. The laser mark 321 has the biggest and the laser marking 324 the smallest distance (arrow 327 and 328) from the optical axis 306, as illustrated by the dashed guides 329 and 330 in the form of circuit segments. To equalize the image representation to the original (1:1) scale on the monitor, a keystone correction of the imaging is performed in such a way that both laser markings are positioned in distances from the optical axis in the resulting image (block 14 in FIG. 1). The arrangement of the laser markings follows the trapezoidal correction of the square plate 311, since their emigration is a representation of the local scale and the plate itself changed in scale in the image representation reproduction accordingly. If the two laser markings 321 and 324 are positioned in the same distance from the optical axis 306, the reproduction of the plate is equalized in scale and will appear on the monitor screen as a square. If the laser beams are directed in parallel the arrangement of the laser markings corresponds to the arrangement of the laser sources 301 in FIG. 3a. The representation has a total scale of 1:1, if the corresponding distribution (distances) of the laser markings 321 to 326 the dimensional relationships of the source. If the selected laser markings are not arranged in the direction of the tilt, as is has been described above, satisfy the general case of which three, to the reproduction of a non-orthogonal to the optical axis directed object plane. For this example, the marking 325 a laser marking is used in addition for evaluation. Their distance 331 (circuit 332) to the optical axis 306 is between the values of the distances 327 and 328, and also adds to the local scale factor. Even with the use of three laser markings the keystone correction of the image representation shall be equivalent to that all three distances to the original spacing of the laser light sources 301 from the optical axis 306. So that the plate may be 311 inclined arbitrarily with respect to the orthogonal to the optical axis 306. The other laser markings 322, 323 and 326 were not used in the above image representation rectification. But there is also the possibility of optimizing the equalization of its influence by use of laser markings by averaging their influence, or it may such a laser markings, which by the slope of a flat plate to differ materially expected intervals eliminated from further processing.

Figure 4:
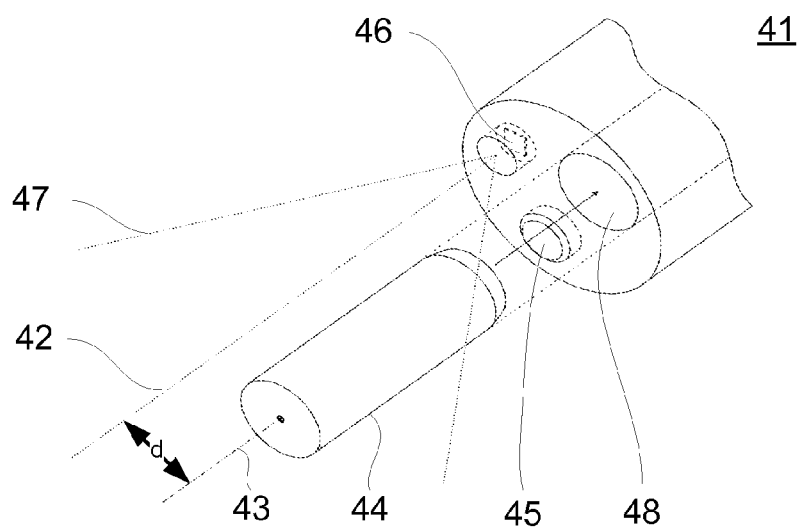
FIG. 4 is a view of a second embodiment of an endoscope according to the invention with a camera in a fixed design.

In FIG. 4 a second embodiment of the invention in the form of a rigid endoscope 40 with a camera is shown. The endoscope 41 in its substantive functions is working in accordance to FIG. 3 and forms but a standard endoscope that needs in no way to be prepared for use with the invention. There are no special means to be provided for the generation of laser light. The required features are realized by the temporary insertion of the laser source into the working channel of the endoscope used. In this case, the insertion of the laser source during use of the endoscope is performed from the (proximal) side facing the operator. Since the working channel is a precision guidance system, an accurate alignment of the laser beam is parallel to the optical axis ensured without special effort.

In FIG. 4 a miniature digital camera 46 with the optical axis 42 has an aperture angle 47. Its optical axis 42 is directed in parallel to a laser beam 43 having a distance d. The laser beam originates from a laser light source 44, having a cylindrical housing that in its external dimensions is adapted to the internal dimension, i.e. the internal cross section, of the working channel 48 of the endoscope. Since the working channel 48 has a uniform cross-section, it forms a guide for the housing of the laser light source 44, which may be used at any level within the working channel. Thus, the laser light source may be temporarily introduced into the working channel from the (proximal) operator side in coordination with other activities, when other tools are not in use. Thus the working area may be inspected and transferred for external inspection in a given scale to ultimately obtain an adapted repair element to be fixed to the working area. Moreover, on distal end of the endoscope 41 a source of light 45 formed by white LEDs is provided which serves to illuminate the working area.

Figure 5:
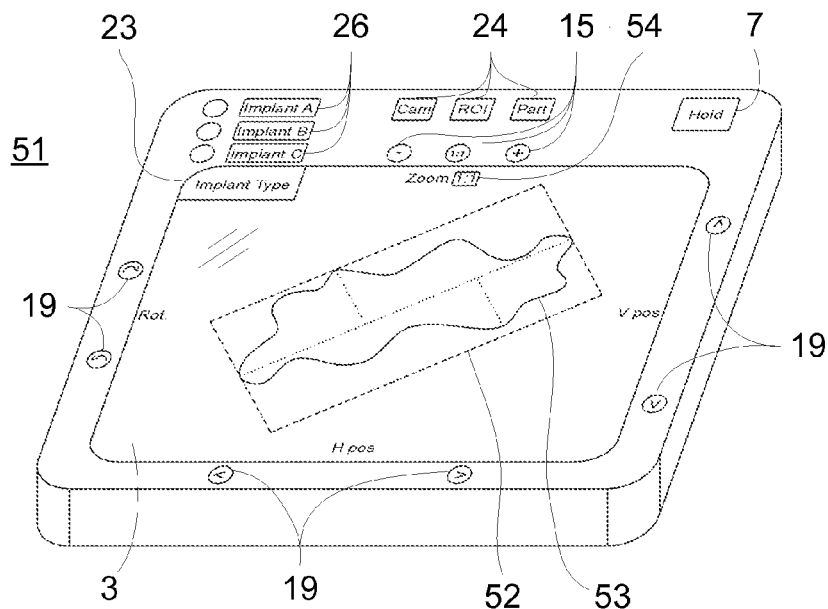
FIG. 5 is a perspective view of the image representation display control unit as part of a monitor according to FIG. 1 and FIGS. 6a and b are perspective schematic representations of further embodiments of the invention.

When reproduced in FIG. 5 detailed view of the image representation display part of the system of FIG. 1 a so-called tablet PC 51 is used, which has a touch monitor display and an appropriate programming. (The programming also includes the scope of the functions shown in FIG. 1, wherein the external elements, such as the camera and light sources may be controlled via corresponding USB interfaces.) The display of the tablet PC 51 forms the entire upper surface area of the device, with the controls shown in the rendered image representation inserted and may be operated by touch. The display 3 according to FIG. 1 only fills a portion of the display of the Tablet PC 51. On the display of this monitor 3 is shown a rectangular repair element 52 with respect to a damaged area 53 of the working field. Furthermore, various actuation elements are displayed, whose function correspond to those described with system shown in FIG. 1. They may be operated by touch. These functions are the following: release 7, standard setting 15, superimposition unit 23, display selection switch 25 and the position switch 27. Furthermore, in the monitor region has a function of the components type display unit 24 is realized which the type of a—indicating to the elements catalogue storage 20 according to figure out a selective element 52 the type—as previously described. In the element 52 may be, for example to a surgical mesh which serves to cover the defected portion 52 forming hernia. In any setting, the scale bar. Although done virtually, via the switch 25 with an additional selection (for example according to the manufacturer or thickness) may be made. About the positions selection switch 27, the representation of the element 52 may be moved horizontally or vertically in order to optimize the adjustment solution or control. This may additionally performed via the selector switch 25, the selection being made by representing the selection relied on the ROI—as the empire on the basis of image representation content criteria selected area in the image representation of the workspace—to be controlled.

In case of a selection of a representation in original (1:1) scale on the scale setting 15, adjustment with an original item that is placed on the monitor screen of the tablet PC may be performed. This may be an individual blank, without requiring a direct access to the surgical area required, so that any excessive stress of the patient is avoided. The PC 51 forms—in an alternative embodiment—a monitor having an independent power supply and being connected via a radio interface with the rest of the system. In embodiment the PC monitor may be used close to the environment where the shape adaptation of a working element has to be performed.

Figure 6A:
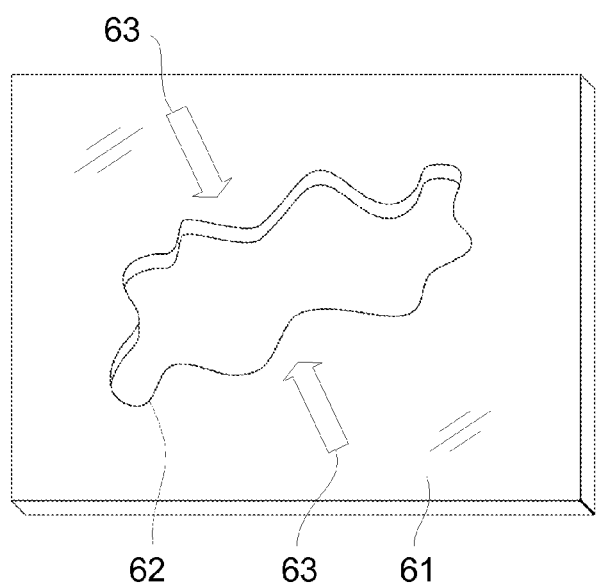

In FIGS. 6a and b further embodiments of the invention are shown in perspective representation. FIG. 6a again shows a template 61 again, which may be used to exclude a portion of a working area directly inaccessible from a working process. The template may be prepared externally by means of the invention. For example, an adjustment of the opening 62 is to be generated within a damaged area to be exclusively achieved during a subsequent machining. This may be the case during the addition of material by means of laser welding within a damaged area. In addition, markings 63 may be provided, which allow a precise orientation and are especially useful, especially when the working field is under endoscopic observation and the visibility is adequately limited. In this example a stencil may transferred in a rolled-up configuration being fed through the working channel of the endoscope to the working area.

Figure 6B:
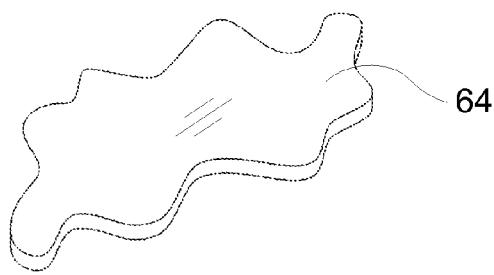

In FIG. 6b an element 64 and corresponding element 64 of a positive form and adhesive capability are shown. This may for example be a surgical adhesive on a backing layer.

The invention claimed is:

1. An image processing system comprising:
   an optical camera with a large depth of field, a digital image sensor, a laser light source generating an information representative of a geometric distance in the form of a pattern, which is detected and processed with the image data captured by the camera, image memory means (9) and a monitor (3) for reproducing the captured image data, wherein the camera (1) having a separator (8) downstream connected thereto which separate the information representative of a geometric distance from the rest of the image data, the separator (8), having an evaluator (13) downstream connected thereto which determine and output physical distance data from the information representative for geometric distance, an actuator (14) for varying the size of the reproduced image on the monitor (9) in the manner of a digital zoom, controlled by the geometric distance data as an input variable, for adjusting the size of the image representation on the monitor (3) in accordance with a scale factor, the physical distance data being included as a multiplier, such that an object contained in the picture data having a physical size corresponding to the physical distance data it is reproduced on the monitor in a size, which is defined by the preselected scale factor, wherein means are provided for generating several laser markings arranged around the optical axis of the camera (1) in symmetric positions, and wherein the image processing system further inhibits those laser markings from further processing within the data of the image representation, that are detected in a position differing from the symmetry position with respect to the optical axis of the camera by more than a predetermined amount.

2. The system of claim 1, wherein the information representative of a geometric distance within the image captured by the camera (1) is at least one laser marking generated by a beam from the laser source (4) directed in a defined direction with respect to the optical axis of the camera (1), wherein the distance between two laser markings or the distance between a laser marking and the optical axis of the camera (1) is the information representative of a geometric distance.

3. The system of claim 1, wherein for an object plane arranged in a non orthogonal direction with respect to the optical axis of the camera, wherein the image processing system adjusts the image representation on the monitor with a locally variable scale factor—corresponding to a trapezoidal or keystone correction—such that the resulting locally relevant scale factors for the image representation are interpolated between the positions of at least two known scale factors derived from the respective data representative for a geometric distance and are accordingly extrapolated outside the known scale factors.

4. The system of claim 1, wherein the separator (8) is provided for determining the difference of the data of two images representations following each other in immediate succession during an on and an off state of the laser light source (4), to highlight the laser markings for further evaluation while the rest of the image representation is reduced in its intensity.

5. The system of claim 1, wherein means are provided for switching off or reducing the intensity of lightings means (11) for the object illumination during the detection of the laser markings.

6. The system of claim 1, wherein a comparator is provided for a form or size comparison of an element or implant to be introduced into a working or surgical field respectively with the image representation of the work or surgical field in which the element or implant is to be inserted is set to the same scale as the image representation of the element or implant.

7. The system of claim 1, wherein for a form or size comparison, of a physical element or a physical implant to be introduced into a working or a surgical field respectively with the image representation in the original scale of the working or surgical field in which the element or implant is to be inserted a monitor display is provided having a supporting surface extending substantially horizontally for direct physical contact with the element or implant.

8. The system of claim 1, wherein storage means are provided for the scaled superimposing (22) of an image representation of an element or an implant to be inserted into a working or a surgical field respectively with an image representation of the working or surgical field, whereby the image representation of the working or surgical field and image representation of the element or implant are in the same scale, and further shifting or rotation means are provided (26) by means of which the image representation of the element or implant may be displaced in its position on the monitor display (3) in its position with respect to the working or surgical in order to improve its geometric interaction with the working or surgical field respectively.

9. The system of claim 8, wherein downstream connected to said storage means for image representation are a form discriminator (16) are provided by partial image representation, wherein the selection is made according to a predetermined criterion from the recorded image representation data and highlighting selected elements into an image representation data summarized as content-based image representation description based on a selection of elements basing on visual features.

10. The system of claim 9, wherein the shape and/or dimensions and visual characteristics of the range of the selected picture elements summarized a selection criterion for the working or operation range to be introduced element or implant or aid in a downstream manner of a catalogue organized memory (20) form in which they are stored as a content-based comparison illustrations suitable or appropriate shape feature identifications.

11. The system of claim 10, wherein a comparator (18) form the basis of a size and/or shape similarity criterion are provided to the output of the shape and/or the type of an element or implants or resource due to the size and/or similarity criterion in an organized way to store a catalogue (20) for outputting an image representation, or to address planning and data-type designation.

12. The system of claim 1, wherein the laser light source (44) is mounted in such way that the laser beam passes at least for part of its length through the working channel of a rigid endoscopes (41), laparoscope or similar device.

13. The system of claim 1, wherein the monitor (51) is formed as a separate component, comprising an independent power supply having a data connection via a radio interface to the rest of the system.

* * * * *